(12) United States Patent
Franjic et al.

(10) Patent No.: US 10,828,119 B2
(45) Date of Patent: Nov. 10, 2020

(54) RFID MEDICAL DEVICE CONTROL INTERFACE

(71) Applicants: Kresimir Franjic, Toronto (CA); Kai Hynna, Toronto (CA); Joshua Richmond, Toronto (CA)

(72) Inventors: Kresimir Franjic, Toronto (CA); Kai Hynna, Toronto (CA); Joshua Richmond, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 276 days.

(21) Appl. No.: 15/813,761

(22) Filed: Nov. 15, 2017

(65) Prior Publication Data

US 2018/0071042 A1    Mar. 15, 2018

Related U.S. Application Data

(63) Continuation of application No. 14/873,814, filed on Oct. 2, 2015, now Pat. No. 9,833,294.

(51) Int. Cl.

| A61B 34/00 | (2016.01) |
|---|---|
| A61B 34/32 | (2016.01) |
| A61B 90/98 | (2016.01) |
| B25J 9/16 | (2006.01) |
| A61B 17/00 | (2006.01) |
| A61B 34/20 | (2016.01) |

(Continued)

(52) U.S. Cl.
CPC .............. *A61B 34/74* (2016.02); *A61B 34/32* (2016.02); *A61B 90/98* (2016.02); *B25J 9/1694* (2013.01); *B25J 9/1697* (2013.01); *A61B 1/00059* (2013.01); *A61B 1/00149* (2013.01); *A61B 1/045* (2013.01); *A61B 2017/00973* (2013.01); *A61B 2034/2055* (2016.02); *A61B 2034/741* (2016.02)

(58) Field of Classification Search
CPC ......... A61B 90/98; A61B 34/20; A61B 90/90; A61B 2034/2051; A61B 2034/2059; A61B 34/74; A61B 34/32; A61B 1/00149; A61B 2034/741; A61B 1/045; B25J 9/1697; B25J 9/1694
See application file for complete search history.

(56) References Cited

U.S. PATENT DOCUMENTS

| 7,994,920 B2 * | 8/2011 | Hatfield | G06K 19/07345 340/5.6 |
|---|---|---|---|
| 2005/0242950 A1 * | 11/2005 | Lindsay | G06K 19/0717 340/539.26 |

(Continued)

*Primary Examiner* — Jason Holloway
(74) *Attorney, Agent, or Firm* — Ridout & Maybee LLP (57) ABSTRACT

A medical navigation system is provided for controlling medical equipment during a medical procedure. The medical navigation system includes a passive radio frequency identification (RFID) tag, an RFID sensor for detecting the passive RFID tag, a controller coupled to the RFID sensor, and a robotic arm having an end effector and controlled by the controller. The RFID sensor provides a signal to the controller indicating presence of an activated passive RFID tag. The passive RFID tag has an antenna, an RFID circuit, and a switching device coupled to the RFID circuit for activating the passive RFID tag. The passive RFID tag is used to control a payload attached to the end effector.

20 Claims, 8 Drawing Sheets

(51) Int. Cl.
*A61B 1/00* (2006.01)
*A61B 1/045* (2006.01)

(56) References Cited

U.S. PATENT DOCUMENTS

| | | | |
|---|---|---|---|
| 2007/0120682 A1* | 5/2007 | Rea | G01S 13/878 340/572.8 |
| 2010/0026456 A1* | 2/2010 | Cline | A61B 1/00059 340/10.1 |
| 2010/0123581 A1* | 5/2010 | Hatfield | G06K 19/0716 340/572.3 |
| 2011/0037565 A1* | 2/2011 | Skirble | G06Q 10/087 340/8.1 |
| 2013/0138599 A1* | 5/2013 | Mangione-Smith | A61B 6/12 706/52 |
| 2016/0361128 A1* | 12/2016 | Seeber | A61B 90/30 |
| 2017/0116446 A1* | 4/2017 | Sample | G06Q 30/0251 |

\* cited by examiner

FIG. 6

RFID MEDICAL DEVICE CONTROL INTERFACE

CROSS-REFERENCE

The present application is a continuation of U.S. patent application Ser. No. 14/873,814, filed on Oct. 2, 2015. The contents of which are incorporated herein by reference.

TECHNICAL FIELD

The present disclosure is generally related to medical procedures, and more specifically to an RFID medical device control interface.

BACKGROUND

Port-based surgery allows a surgeon, or robotic surgical system, to perform a surgical procedure involving tumor resection in which the residual tumor remaining after is minimized, while also minimizing the trauma to the intact white and grey matter of the brain. In such procedures trauma may occur, for example due to contact with the access port, stress to the brain matter, unintentional impact with surgical devices, and/or accidental resection of healthy tissue.

Minimally invasive brain surgery using access ports is a recently conceived method of performing surgery on brain tumors previously considered inoperable. To address intracranial surgical concerns, specific products such as the NICO BrainPath™ port have been developed for port-based surgery.

Figure 1:
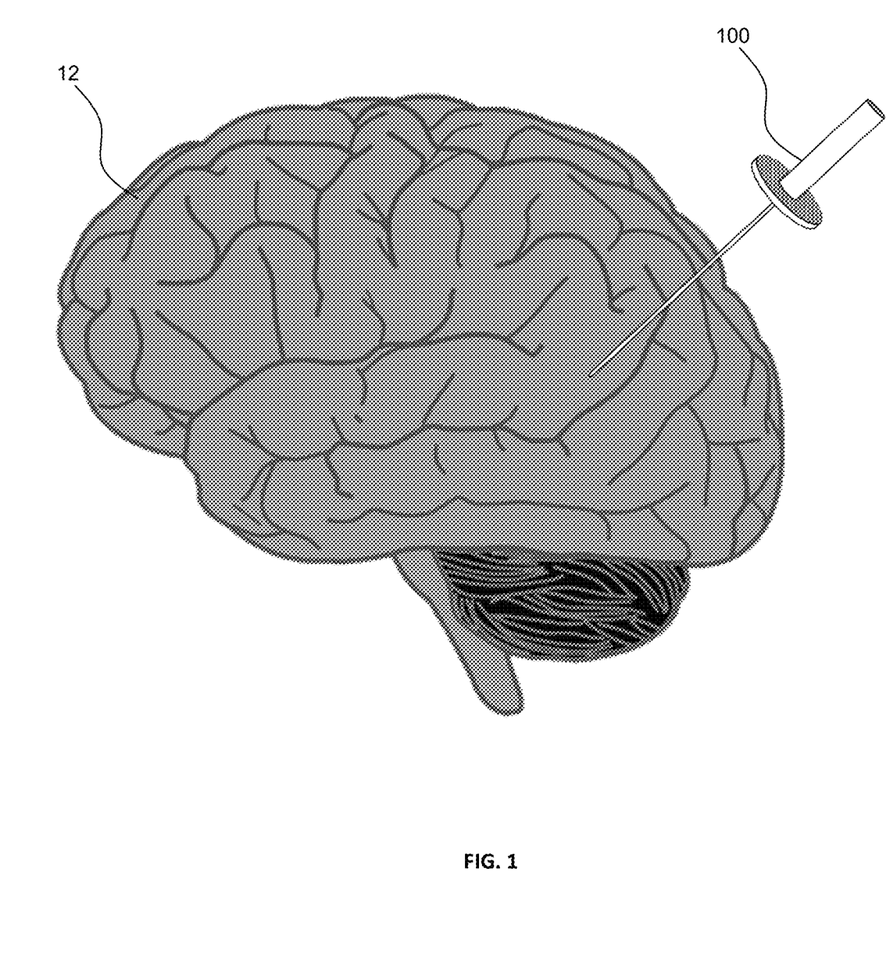
FIG. 1 illustrates the insertion of an access port into a human brain, for providing access to internal brain tissue during a medical procedure.

Referring to FIG. 1, the insertion of an access port into a human brain is shown for providing access to internal brain tissue during a medical procedure. In FIG. 1, access port 100 is inserted into a human brain 12, providing access to internal brain tissue. Surgical tools and instruments may then be inserted within the lumen of the access port in order to perform surgical, diagnostic or therapeutic procedures, such as resecting tumors as necessary.

As seen in FIG. 1, port 100 comprises of a cylindrical assembly formed of an outer sheath. Port 100 may accommodate an introducer which is an internal cylinder that slidably engages the internal surface of port 100. The introducer may have a distal end in the form of a conical atraumatic tip to allow for insertion into the sulcal folds of the brain 12. Port 100 has a sufficient diameter to enable bimanual manipulation of surgical tools within its annular volume such as suctioning devices, scissors, scalpels, and cutting devices.

Figure 2:
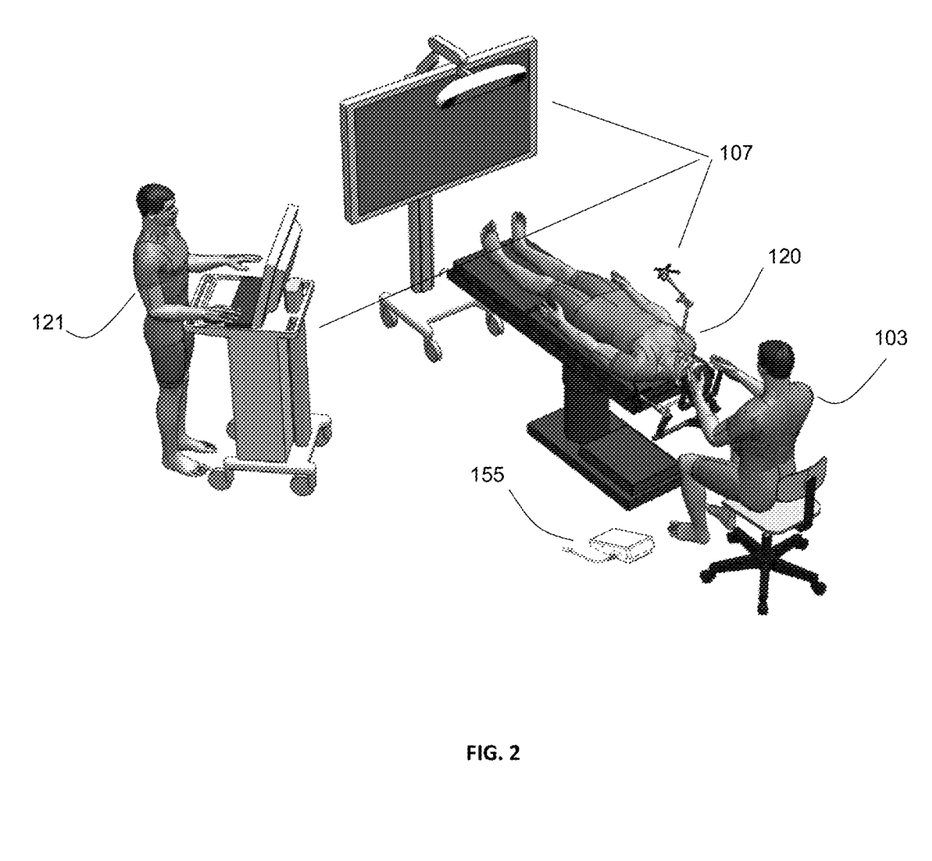
FIG. 2 shows an exemplary navigation system to support image guided surgery.

Referring to FIG. 2, an exemplary navigation system is shown to support surgery, which in one example could be a minimally invasive access port-based surgery. As shown in FIG. 2, a surgeon 103 conducts surgery on a patient 120 in an operating room (OR) environment. A navigation system 107 comprising an equipment tower, tracking system, displays and tracked instruments assists the surgeon 103 during his procedure. An operator 121 is also present to operate, control and provide assistance for the navigation system 107.

A foot pedal 155 is placed near the surgeon's foot and is utilized to actuate different elements during the procedure. For example, foot pedal 155 may be used to lift or lower the surgical bed, or control zoom of the navigation system 107 or tracking system. In certain instances, multiple foot pedals may be deployed.

Conventional foot pedals used by a surgeon during a surgical procedure, particularly when multiple foot pedals are used, can be a distracting, given the surgeon must sometimes remove his focus from the surgical field of interest, resulting in the surgeon having to reorient himself when his attention is returned. Further, by manipulating the foot pedal, the surgeon may lose concentration and/or focus of the surgical procedure at hand. Further, conventional foot pedals have wires attached thereto for communication and power supply, which creates tripping hazards. There is an opportunity for improvement in the area of surgical controls. There is a need for mechanism to provide improved functionality and replacement of the foot pedal and other conventional medical control devices. There is a need for a medical control device that can be used in multiple locations, is not expensive to manufacture, does not create hazards in the operating room, and can be manufactured in various forms.

SUMMARY

One aspect of the present description provides a medical navigation system for controlling medical equipment during a medical procedure. The medical navigation system includes a passive radio frequency identification (RFID) tag, an RFID sensor for detecting the passive RFID tag, a controller coupled to the RFID sensor, and a robotic arm having an end effector and controlled by the controller. The RFID sensor provides a signal to the controller indicating presence of an activated passive RFID tag. The passive RFID tag has an antenna, an RFID circuit, and a switching device coupled to the RFID circuit for activating the passive RFID tag. The passive RFID tag is used to control a payload attached to the end effector.

The switching device may also be coupled to the antenna and includes a mechanical switch that connects and disconnects the antenna from the RFID circuit, thereby activating and deactivating the passive RFID tag.

The antenna may instead or further be coupled to the RFID circuit and the passive RFID tag transmits a first identification (ID) and the switching device includes a mechanical switch that changes the transmitted ID to a second ID when the switch is pressed.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

The use of switches in presently performed surgical procedures is a useful feature for convenient control of the surgical devices and systems involved. However, presently available actuation devices result in inefficiencies that must be overcome by the surgeon and/or surgical team. Examples of such inefficiencies will be described below.

There are many sources of ergonomic issues encountered during common surgeries shown using foot pedals. The use of foot pedals creates problems associated with physical, perceptual, and cognitive use. The present application aims to address these problems and others associated with presently used actuation or control devices.

In an ideal surgical procedure, a surgeon will minimize the amount of time in which his focus is away from the surgical site of interest. This includes minimizing the time during which the surgeon is not viewing the surgical site of interest as well as the time during which the surgeon is not in the bimanual procedural position or any other potential instance which can be avoided to minimize the time required for the surgery. When utilizing a foot pedal switch as described above, inefficiencies can be attributed to the situations described below.

Figure 3:
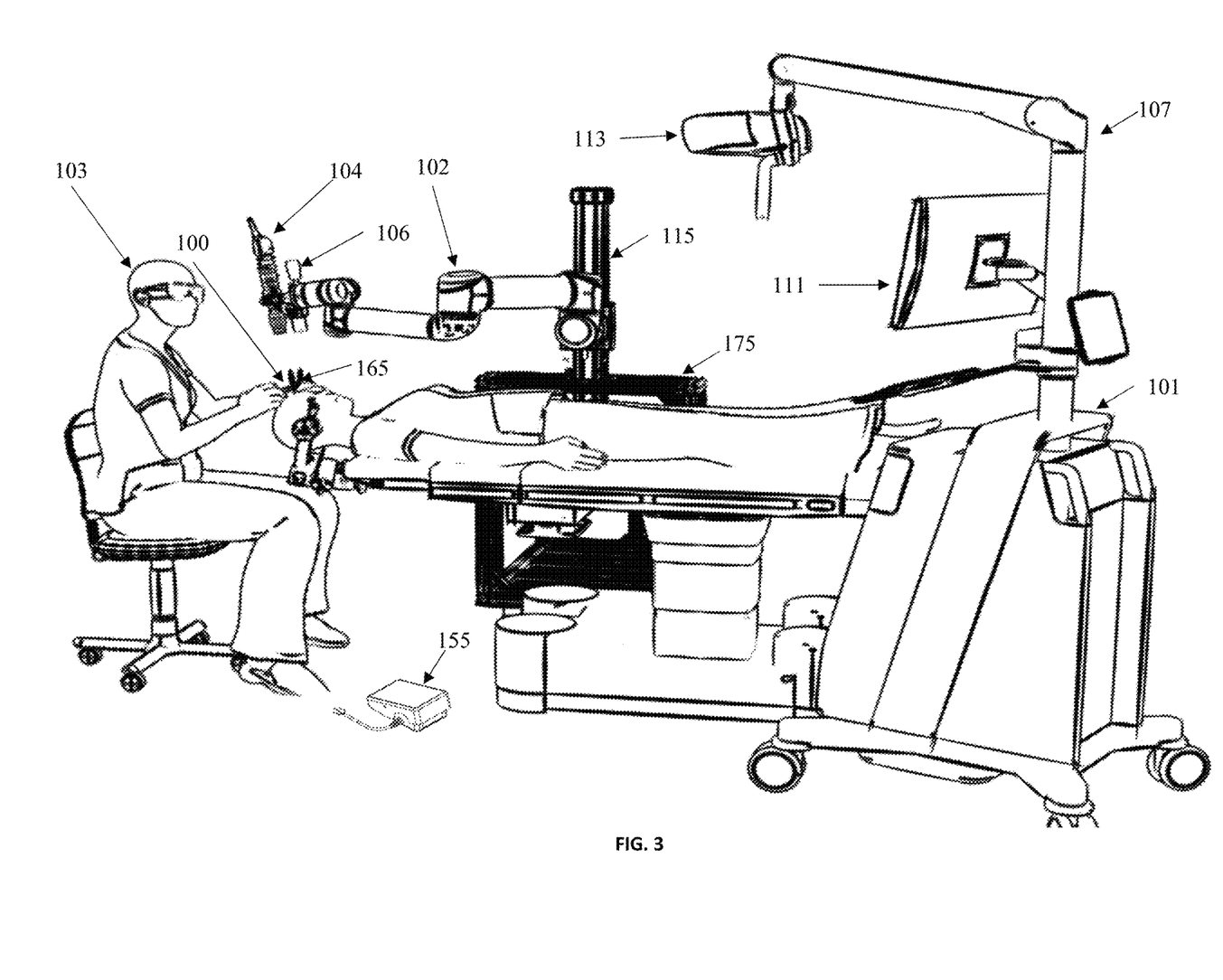
FIG. 3 is a diagram illustrating components of an exemplary surgical system used in image guided surgery.
Figure 4:
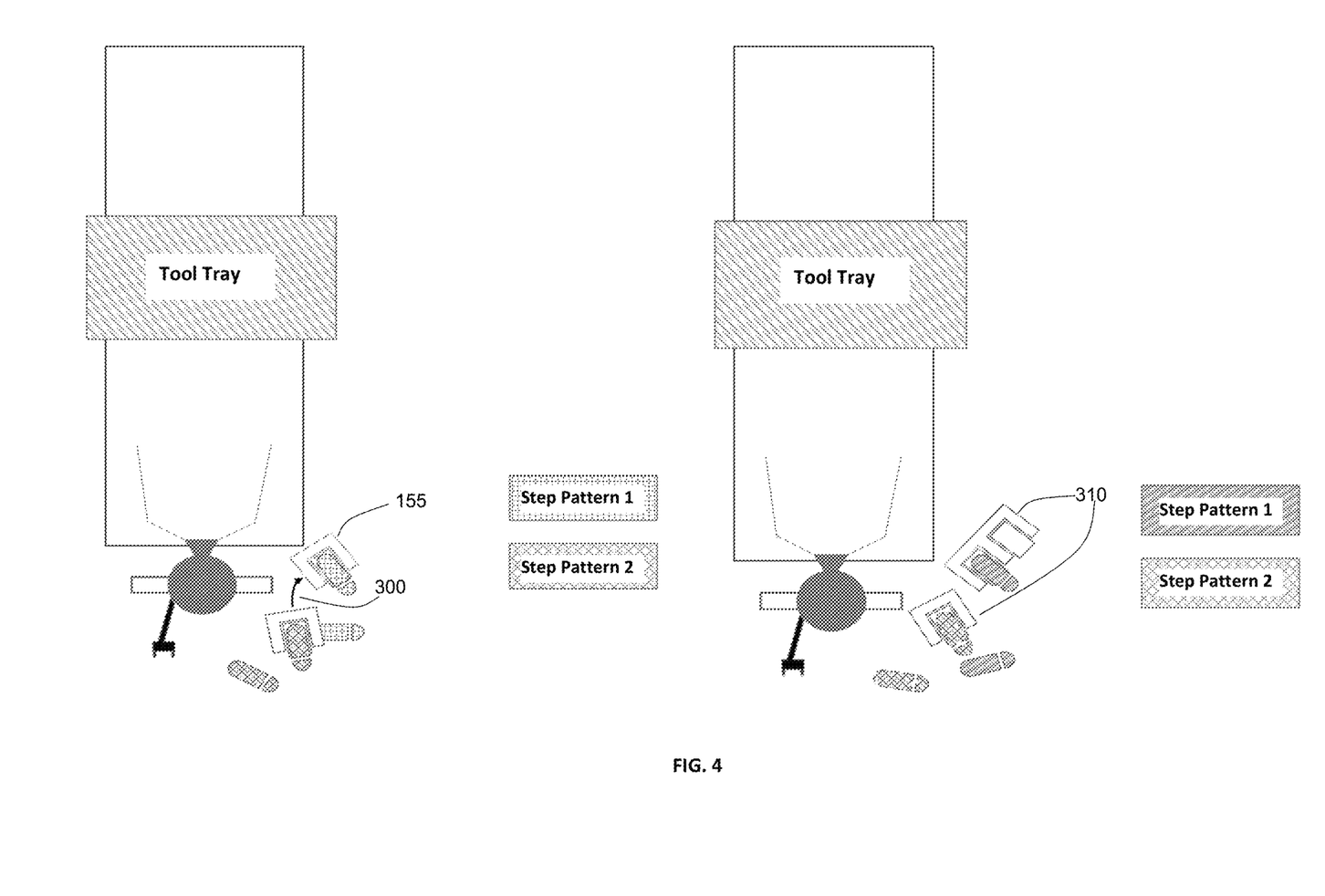
FIG. 4 illustrates various foot pedals and foot positioning of surgeons during commonly performed neurosurgeries.

Referring now to FIG. 3, a diagram is shown illustrating components of an exemplary surgical system such as the medical navigation system 107 used in port based surgery. Reference is also made to FIG. 4, which shows various foot pedals and foot positioning of a surgeon during commonly performed surgeries. In one instance the surgeon may have to reposition one or more foot pedals 155 when he changes his orientation relative to the patient during surgery, indicated by reference 300 (FIG. 4). When this occurs, the surgeon's focus is removed from the surgical area of interest to correctly reposition the foot pedal 155. In addition, this may also require the surgeon to remove his tools from the bimanual procedural position as well.

During a medical procedure a surgeon may have to use the foot pedals 155 in an inopportune (e.g., non-ergonomic) position. Various operating stances can require the surgeon to position himself awkwardly and therefore make the use of a pedal inefficient and difficult to do with accuracy. In one example, the surgeon may be leaning over the patient requiring the surgeon to fully extend his leg and even have to stand on his toes. It is apparent that in such a stance the resulting positioning of the foot would make it difficult for the surgical personnel to operate the foot pedal because in such a position the heel of the foot would be elevated from the ground. Even if the foot is located on the ground, but is fully extended, the ball of the foot will be difficult to use in a flexion as it would be required for stability of the surgeon. Therefore, using the foot to operate the foot pedal in such a position would reduce the amount of precision when engaging the foot pedal through a plantar flexion movement. This situation may also require the surgeon to move the pedal(s) 155 positioning on the floor of the operating room resulting in increased time required for the surgical procedure and hence decreasing efficiency of the operation.

The surgeon may also have to use multiple foot pedals 155 during a surgical procedure requiring him to differentiate between foot pedals through proprioception, estimated foot pedal placement knowledge, and his sense of touch as opposed to knowing with a greater certainty the location of the pedal 155 he wants to actuate relative to his foot position. This estimation of pedal 155 location using touch and proprioception may also be inhibited by the wearing of shoes. If the surgeon is unable to locate the pedal 155 using the three senses mentioned, the surgeon will be again required to remove his focus from the surgical site of interest and his tools from the bimanual procedural position in order to do so. It should be noted that this is a consequence of free placement of the pedals 155 on the floor, since the pedals 155 aren't placed at a "known" relative position (e.g., a position relative to the surgical bed or area of interest) that the surgeon could intuitively find using touch or proprioception knowledge in combination with previous surgical experience. Other issues in locating and engaging the foot pedal(s) 155 may be caused when the foot pedal 155 is placed under the surgical bed, where it would be out of site of the surgeon and may require the surgeon to spend more time locating the pedal(s) 155 as opposed to being positioned in clear site.

At points during the surgery the surgeon may have to stand and utilize motor functions in both his arms and legs to position a medical device and actuate it simultaneously using the foot pedal 155 respectively. This may be an inefficient way for the surgeon to operate a device as the simultaneous actuation of a foot pedal 155 and precise arm movement is not an intuitive function for most individuals.

The use of a foot pedal 155 in a surgical procedure may also impose additional wiring on the floor of the surgical suite, resulting in increased tripping hazards in the operating room, which are dangerous and may cause serious harm to the patient if surgical personnel were to trip over such wiring.

An alternate procedural element actuation device utilizes a tool with an attached or integrated switch such as the Stryker Smart Instruments. When using such a tool, inefficiencies may occur in the following contexts. The tool may have a limit on its available area for a given user interface control containing switches for manipulation of elements used during the surgical procedure. Reasons for such limits relate to the user interface being integrated into the tool as opposed to a separate control user interface. Since surgical tools are precise instruments to be manipulated by the surgeon, their weights, sizes, and overall features greatly affect the dexterity of the surgeon. Therefore, increasing the size of the user interface control area for more numerous and/or larger more easily identifiable and accessible buttons may result in heftier instruments again reducing the precision of the surgeon when using the tool. Additionally, when tools are engaged in minimally invasive surgeries, the tools must be manipulated within a small corridor. In this context increasing the size of the tool may not be feasible as it may occlude the view down the corridor or become too large as to restrict access of the tool into the corridor. Alternate issues are associated with placing an electronic user interface on a surgical tool. The electronics must be designed to withstand commonly used sterilization processes. Viable ways of achieving such an ability to withstand sterilization require the electronics to be bulkier and heavier than their non-integrated counterparts (e.g., the tool without the user interface controller) as sterilization occurs at high temperatures and pressures. Specifically, when sterilizing medical instruments using the autoclaving technique the instruments must withstand temperatures of 121° C.-190° C. and pressures of 15 psi-40 psi.

The manufacture and purchase of tools with built in user interfaces is also problematic. Multiple surgical tools each having a built in user interface (UI), for example, both a resection tool and bipolar pituitary forceps, to be used within a surgical procedure will likely be more costly than having a single surgical glove interface that can be integrated with all potential tools the surgeon may use. An advantage to using a single entity surgical glove interface disclosed herein is that the surgical glove interface may be configured to adaptively switch output selection such that the detection of the tool being used by the system sets the output of each of the buttons, as opposed to having a separate user interface on each medical tool as would be required by a surgical tool with a built in user interface.

When utilizing a kinect based gesture control user interface to control surgical procedural elements, inefficiencies can occur in the following contexts. Such a user interface control requires the surgeon to remove his hands from the bimanual procedural position when performing the gestures required to control the user interface. In addition to this requirement, the surgeon must perform an initial gesture to initiate the Kinect sensors and begin controlling the user interface which in turn increases the time required for the surgery as opposed to being able to constantly control the interface. A consequence of this user interface control system is that the surgeon has to remove his attention from the surgical site of interest (or equivalently a display of the surgical site of interest) when performing gestures to control the system. This results in the surgeon having to directionally reorient himself with the display of the surgical site of interest with respect to the spatial orientation of the patient in the operating room when returning to the bimanual procedural position, which will also result in an increase of the total time of the surgical procedure. Since the Kinect sensor is a detector with an inherent field of view, the surgeon may additionally have to reposition himself away from his surgical procedural stance in order to enter the correct field of view, to gain full control over the functionality of the user interface.

Referring back to FIG. 3, FIG. 3 illustrates a medical navigation system 107 having an equipment tower 101, a tracking system 113, a display 111 (e.g., to show a graphical user interface), an intelligent positioning system 175 and tracking markers 165 used to track medical instruments or an access port 100. Tracking system 113 may be considered an optical tracking device or tracking camera.

In FIG. 3, a surgeon 103 is performing a tumor resection through a port 100, using an imaging device 104 to view down the port at a sufficient magnification to enable enhanced visibility of the instruments and tissues. The imaging device 104 may be an exoscope, videoscope, wide field camera, or an alternate image capturing device. The imaging sensor view is depicted on the visual display 111 which the surgeon 103 uses for navigating the port's distal end through the anatomical region of interest. The foot pedal 155 is located in an accessible vicinity to the surgeon's foot and is utilized to actuate an element used in the procedure.

The intelligent positioning system 175 receives as input the spatial position and pose data of the automated arm 102 and target (for example the port 100) as determined by tracking system 113 by detection of the tracking markers 165 on the wide field camera 106 and the port 100.

The foot pedal 155 is located in an accessible vicinity to the surgeon's foot. Foot pedal 155 may be used to actuate an element used in the procedure such as a neurosurgical drill, an illumination source, automated arm movement, a UI configuration, a resection device, an irrigation device, an imaging procedure, an imaging acquisition, a change of phase during surgery, or any other element requiring actuation during a surgical procedure. Foot pedal 155 may have multiple activation input configurations or modes as described in the following examples.

A first input configuration (or first mode) includes a binary switch mode in which a press of foot pedal 155 causes the foot pedal 155 to output a signal which actuates the state of a procedural element from "on" to "off" position. A second input configuration (or second mode) is a variable switch mode in which the output signal of the foot pedal is proportional to the degree of force applied to the pedal by the user. A third input configuration (or third mode) may be a multiple switch mode in which a press of the foot pedal cycles the element through various modes of function (i.e. modes of function of the element). It should be noted that all switches mentioned in this disclosure can be formed of any mechanism to allow for control of or actuation of a device.

These input configurations can also be implemented in combinations provided the system utilizes more than one foot pedal as shown as 310 in FIG. 4. For example, given two foot pedals as shown in FIG. 4, combinations can be two binary switches, in which the combined activation of both foot pedals can result in an alternate output from the output of each foot pedal activated individually. Another example combination using two foot pedals can be two multiple switch modes in which the foot pedal outputs when both are activated can be different from when the pedals are activated individually. Another example using two foot pedals would be a binary switch and a multiple switch in which the output of the activation of both foot pedals may be different than when the pedals are activated individually.

According to one aspect of the present description, the finger of a surgeon may be used with a modified passive RFID tag that only activates when the device is pressed (e.g., when a button on the device is pressed).

Figure 5A:
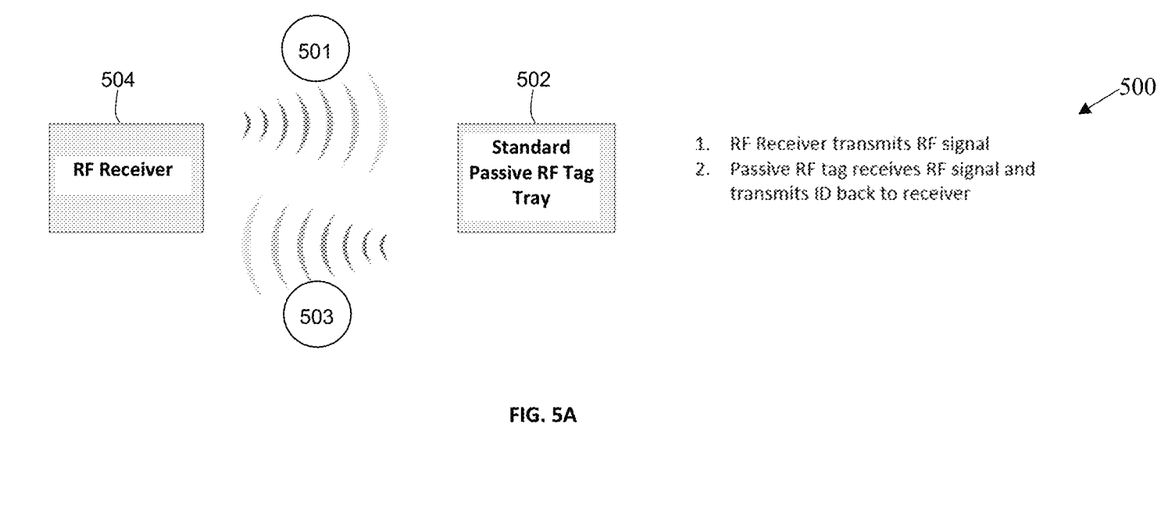
FIG. 5A illustrates operation of a conventional passive RFID tag.

Referring to FIG. 5A, operation of a conventional passive RFID tag is shown, indicated by reference 500. A conventional passive RFID tag 502 activates when receiving an RF signal (indicated by reference 501) from an RFID reader or receiver 504. The RF signal 501 powers the passive tag 502, which then responds with its identification (ID, indicated by reference 503), which is received by receiver 504.

Figure 5B:
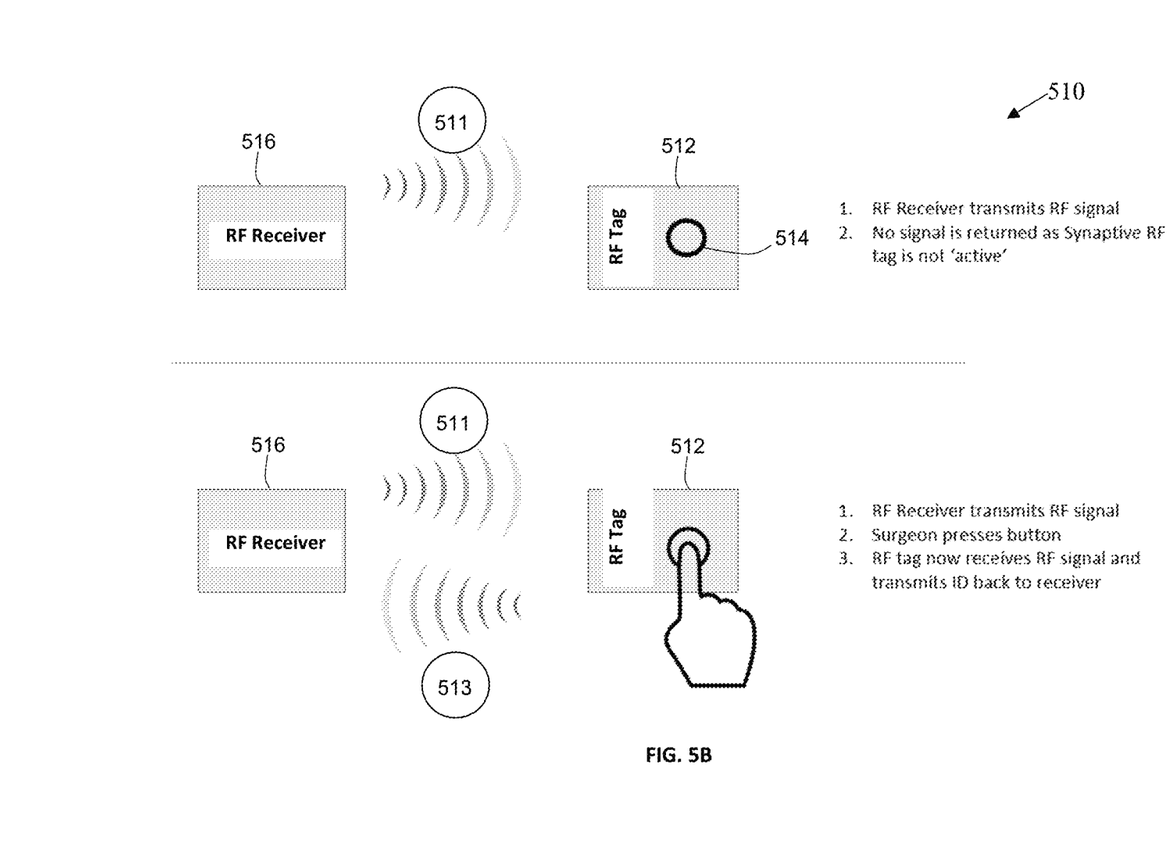
FIG. 5B illustrates operation of an RFID medical control device according to one aspect of the present application.

Referring to FIG. 5B, an exemplary operation of an RFID medical control device interface, indicated by reference 510, according to one aspect of the present application is illustrated. The conventional passive RFID tag 502 may be modified to change the circuit such that modified passive RFID tag 512 can only respond accurately when a button 514 is pressed. In the top half of FIG. 5B, receiver 516 transmits transmission 511. Button 514 is not pressed, so RFID tag 512 does not respond to RF signal transmission 511. In one example, button 514 may be a mechanical button included in an RFID circuit such that the circuit only functions when the button 514 is pressed. In another example, the button 514 or switching device may take advantage of the finger's capacitance to adjust the frequency properties of the RFID tag 512 so that the RFID tag 512 only reaches the correct transmission frequency when the finger is in contact with button 514. In the bottom half of FIG. 5B, button 514 is pressed, so RFID tag 512 responds to RF signal transmission 511 with ID transmission 513. RF receiver 516 then recognizes the button press as the RFID tag 512 transmits its ID. In another example, the RFID tag 512 may send a first ID when the button 514 is not pressed and a second different ID when the button 514 is pressed.

The button 514 forming part of RFID tag 512 may be applied to any surface, such as a finger, a wrist, a tool, a chair, etc. In one example, the RFID tag 512 may be placed on a pointer tool which, when combined with the tracking mechanisms of the navigation system 507, may provide for movement of the pointer tool to be tracked and function as a virtual mouse for the surgeon to move a mouse on a screen, when the button 514 is activated. In another example, the RFID tag 512 may be a simple disposable sticker that could be applied pre-surgery.

Figure 5C:
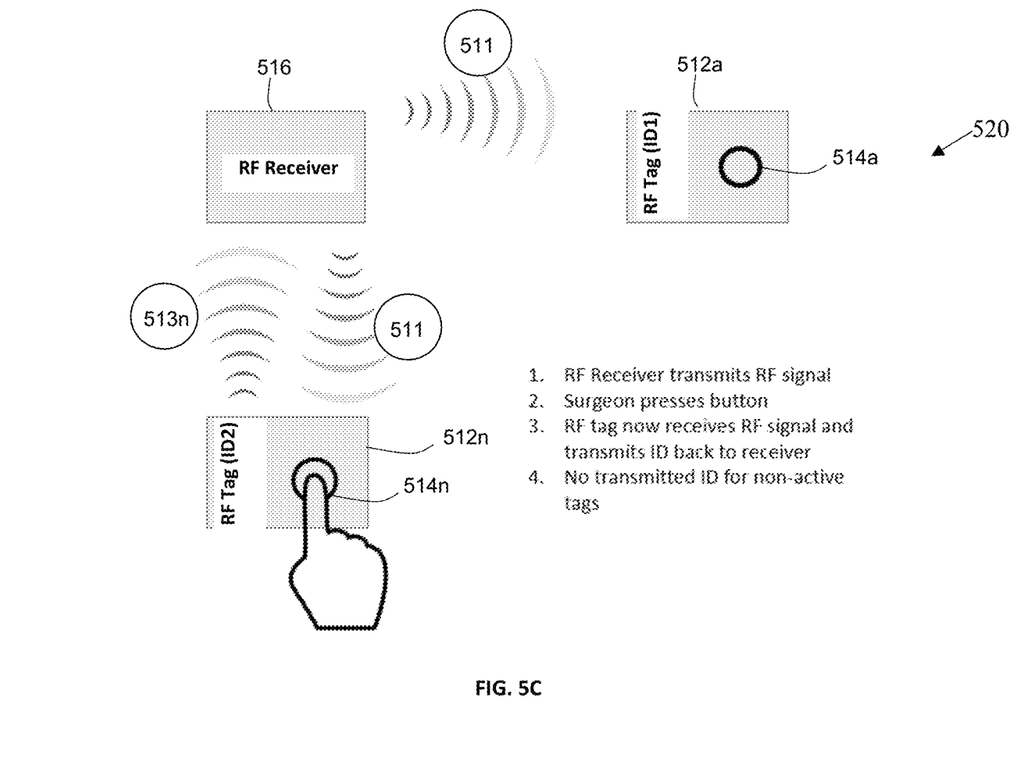
FIG. 5C illustrates operation of multiple RFID medical control devices of FIG. 5B.

FIG. 5C illustrates operation of multiple RFID medical control devices, indicated by 512*a* . . . 512*n*, or collectively as 512. While two RFID medical control devices 512*a* and 512*n* are shown in the example, any suitable number may be used according to the design criteria of a particular application, as denoted by n in 512*n*. Multiple RFID tags 512*a-n* may be used within the same surgery. Given the flexibility of using a sticker form of the RFID tag 512, surgeons may develop their own preferences on where they stick the tags 512.

In FIG. 5C, receiver 516 transmits transmission 511. Button 514*a* is not pressed, so RFID tag 512*a* does not respond to RF signal transmission 511. However, button 514*n* of passive RFID tag 512*n* is pressed, so RFID tag 512*n* responds to RF signal transmission 511 with ID transmission 513*n*. RF receiver 516 then recognizes the button press as the RFID tag 512*n* transmits its ID. In one example, the RF receiver 516 is coupled to navigation system 507 and the system 507 may be configured to interpret a positive command only when more than one tag 512 is active. For example, there may be two RFID tags 512*a* and 512*b* and the user may have to press the button 514 on each of RFID tag 512*a* and 512*b* before a corresponding function of navigation system 507 is activated.

In another example, the RFID tags 512 may be made active by adding a battery. While this would make the RFID tag 512 more expensive, it would reduce the signal levels of the RF receiver 516, which might be desirable in some applications.

The use of the RFID tag 512 described in connection with FIGS. 5B-5C may eliminate the need for the surgeon to utilize his eyes to locate a switch, such as in the case of foot pedals 155 and the tool integrated controller user interface as described above, as the RFID tag 512 may be located in an easily accessible vicinity to the surgeon's hand throughout the performance of the surgery. In contrast, both the use of the foot pedal and the tool integrated user interface would require the surgeon to estimate the relative location of the switches on the foot pedal and the tool respectively relative to the engaging body part (e.g., the surgeon's foot and finger(s) respectively) in addition to using proprioception. The use of the RFID tags 512 may also substantially reduce or eliminate the need for the surgeon to retract the tools from the bimanual procedural position prematurely during the surgery to allow for control of the user interface, such as when using the Kinect user interface controller.

As mentioned above, having a tool integrated user interface controller decreases the tool's precision as a result of various dimensional considerations such as size of an access corridor in a minimally invasive surgery, increased dimensions of the tool, such as weight, height, length, width, etc. In contrast, when using the passive RFID tag 512, the interface may be situated on the palm of the surgeon, and therefore adding or reducing the features of the interface, such as a touch pad (described below), buttons, etc., do not affect the precision of the tool being used. In addition, the palm of a surgeon will generally have more available space in comparison to a surgical tool handle (e.g., without integrated user interface controller) allowing for a larger user interface controller area.

When presently performing surgery many surgeons utilize a foot pedal while simultaneously maneuvering their surgical tools in the surgical area of interest, for example when resecting a tumor a surgeon will control the removal rate of the resection device with his foot and the resection device's position in the surgical area of interest with his hand, inclusive of the arm. In general, a surgeon's fingers are more agile and precise in applying force than his foot. The passive RFID tag 512 takes advantage of this fact and allows both the positioning of the tool and its control user interface (where passive RFID tag 512 is used for this purpose) to be managed by the hand of an individual surgeon. Also, since passive RFID tag 512 does not have to be located on the ground, the additional hazardous wiring mentioned above will be alleviated in the operating room.

Figure 6:
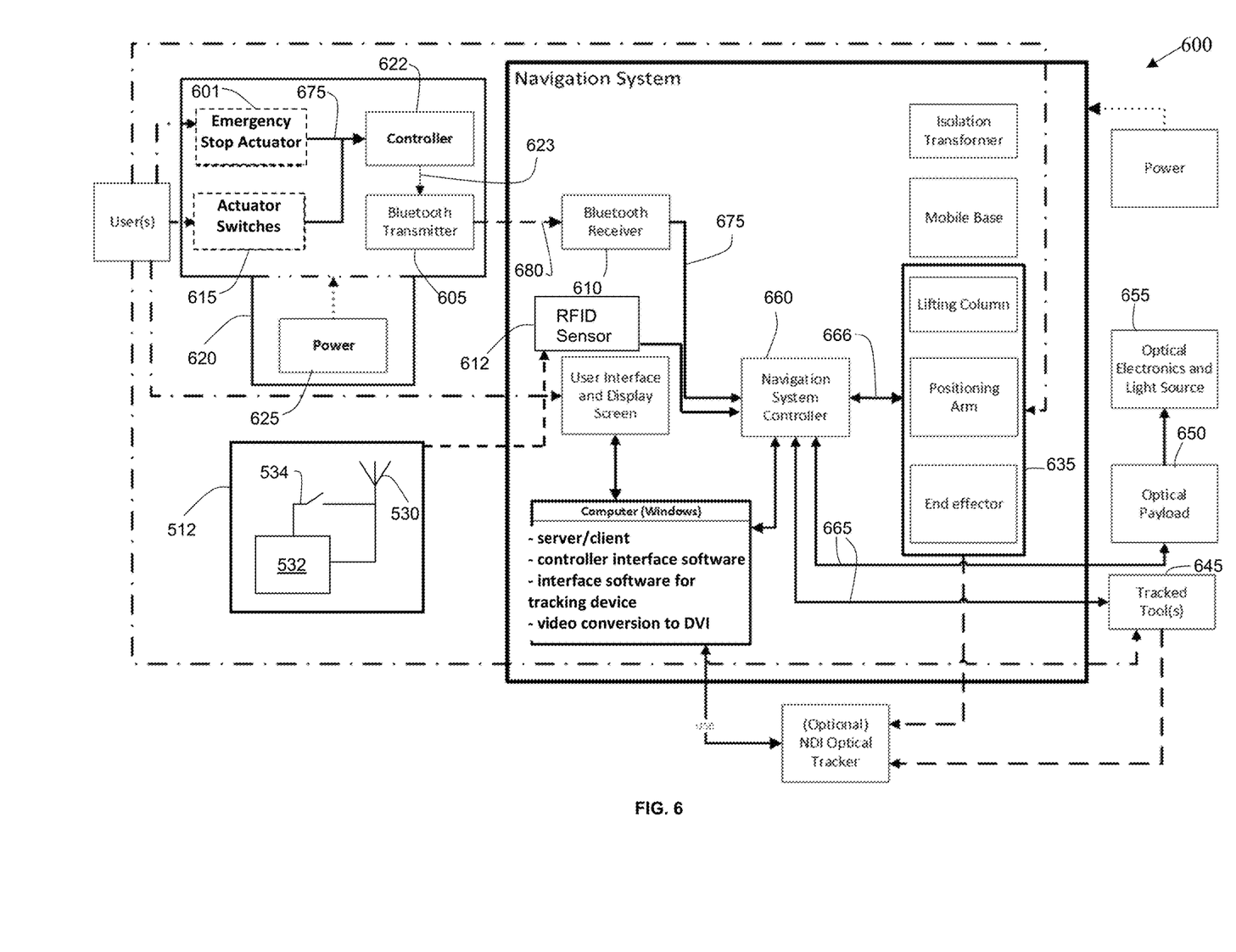
FIG. 6 is block diagram showing an exemplary navigation system or surgical system which may be used with the RFID medical control device shown in FIGS. 5B and 5C.

Referring to FIG. 6, a block diagram is shown illustrating an exemplary medical navigation system 600 that may be used in the systems shown in FIGS. 2 and 3, and may also be used with the RFID tag 512 shown in FIGS. 5B-C. An example embodiment of a medical navigation system 600 inclusive of the RFID tag 512 disclosed herein is provided in FIG. 6 in block diagram form.

FIG. 6 shows part of a medical navigation system 600. The medical navigation system 600 includes a passive radio frequency identification (RFID) tag 512. The passive RFID tag 512 has an antenna 530, an RFID circuit 532, and a switching device 534 coupled to the antenna 530 and/or the RFID circuit 532 for activating the passive RFID tag 512. The medical navigation system 600 further has an RFID sensor 612 for detecting the passive RFID tag 512 and a controller 660 coupled to the RFID sensor 612. The RFID sensor 612 provides a signal to controller 660 indicating presence of an activated passive RFID tag. Depending on the design criteria of a particular application, the switching device 534 may be coupled to both the antenna 530 and the RFID circuit 532 to interrupt the pathway to the antenna 530 or just to the RFID circuit 532 as a means of providing an input to the RFID circuit 532. Likewise, the antenna 530 may be directly coupled to the RFID circuit 532, coupled only through the switching device 534 to the RFID circuit 532, or both, depending on the design criteria of a particular application.

In one example, the switching device 534 may include a mechanical switch that connects and disconnects the antenna 530 from the RFID circuit 532, thereby activating and deactivating the passive RFID tag 512. In another example, the passive RFID tag 512 transmits a first identification (ID) and the switching device 534 includes a mechanical switch that changes the transmitted ID to a second ID when the switch is pressed. In one example, the passive RFID tag 512 may continue to transmit the second ID after the switch is depressed and until the switch is pressed again. In another example, the passive RFID tag 512 reverts to transmitting the first ID when the switch is depressed.

In yet another example, the switching device 534 may include a touch sensor controllable by proximity to human skin. The switching device 534 may adjust frequency properties of the passive RFID tag 512 such that the passive RFID tag 512 operates at an operational frequency when human skin is in contact with the switching device 534.

The medical navigation system 600 has a tracked medical tool 645 that may have the passive RFID tag 512 mounted thereon. In another example, the passive RFID tag 512 may be enclosed in or attached to a sticker such that the passive RFID tag 512 can be adhered to any surface in an operating room environment. In another example, a collar wearable around a finger may have the passive RFID tag 512 enclosed therein or attached thereon. In another example, when the skin comes into close proximity and/or contact with the touch sensor, the antenna 530 may be detuned and the RFID tag 512 may not operate at an operational frequency when the touch sensor is being touched. In other words, the RFID tag 512 may transmit an ID when the touch sensor is not being touched and the RFID tag 512 may stop transmitting the ID when the touch sensor is touched. However, depending on the design criteria of a particular application, the RFID tag 512 may also be configured to not transmit an ID when the touch sensor is not being touched and the RFID tag 512 may begin transmitting the ID when the touch sensor is touched.

In one example, data may be written to the RFID tag 512 during a medical procedure to encode some data such as how many times a certain tool is used (e.g., when the tag 512 is on the tool 645), if the tool is calibrated or not, and/or what procedure was done with the tool. The data to be written to the RFID tag 512 may be provided by the navigation system 600.

In one example, the medical navigation system 600 includes a robotic arm, such as automated arm 102 (FIG. 3) indicated by reference 635 in FIG. 6, controlled by the controller 660. The passive RFID tag 512 may be used to control a payload attached to an end effector of the robotic arm. The payload may be anything from the group such as a camera, an OCT system, an imaging system, an imaging device, a microscopy device, an exoscope, a display device, an optical coherence tomography (OCT) device, a spectrometry device, or any other suitable device. In one example, there may be a plurality of the passive RFID tags 512 in use in an operating room environment. The passive RFID tag 512 may be disposable and/or wearable under a surgical glove. In the case where a plurality of passive RFID tags 512 is used, each of the plurality of passive RFID tags 512 may each have a distinct physical pattern usable to differentiate between the plurality of passive RFID tags 512 using touch.

FIG. 6 illustrates other control devices such as switching input device 620. When a switch 615 is triggered, switch 615 provides a control signal 675, which corresponds to a command to the controller 622. The controller 622 then encodes the control signal 675 into a digital signal 623 and relays this digital signal to the wireless communications interface 605. This signal is then encoded and relayed by the wireless communications interface 605 over a radio frequency wireless communication channel 680 using, for example, Bluetooth protocol. The output signal is then received by a wireless interface 610, which in one example may be a Bluetooth transceiver employing the Bluetooth protocol, and is decoded and relayed to the medical navigation system controller 660. The medical navigation system controller 660 then reads the control signal 675 and outputs the corresponding control signals 665 to the various devices used in the medical procedure. While a Bluetooth protocol is provided as an example, any suitable wireless communications system and protocol may be used to meet the design criteria of a particular application, such as Wi-Fi, irDA, Zigbee, or any other suitable system and/or protocol. Any of the components described in connection with switching device 620 may optionally be integrated into passive RFID tag 512, even power supply 625, which would make passive RFID tag 512 an active RFID tag.

The medical navigation system 600 may further interface with tracked tools 645 and control optical electronics or light sources 655 using control signal 666 provided to the optical payload 650.

An exemplary surgical tool that is commonly utilized in surgery is the bipolar forceps (e.g., electrocautery device), with which a surgeon is able to cauterize vital blood vessels to prevent excessive bleeding. A command that can be actuated using the passive RFID tag 512 would be to activate the forceps for cauterization, such as by applying a voltage across the separated tips. A second commonly used surgical tool would be a resection device. The passive RFID tag 512 can be used to implement commands to this device such as the implemented suction force and whether the device is in tissue removal mode (e.g., tissue removal blade activated) or tissue manipulation mode (e.g., tissue removal blade deactivated). The suction force command will determine at what rate tissue will be resected by the device while the removal mode command will indicate to the device to cut the tissue or not. The resection tool commands are analogous to the third surgical tool, the neurosurgical drill, which may also be controlled by the passive RFID tag 512 by the surgeon. Commands for this device may turn the drill on and off and may also dictate the speed of the drill as to minimize trauma to the patient in the form of vibrational pressure and increase the drill's effectiveness. Another exemplary surgical tool that may be controlled by the passive RFID tag 512 is a Raman imaging probe. The passive RFID tag 512 may send commands via the controller 660 to this device to dictate its acquisition rate, its acquisition area, its acquisition wavelength band, and when it acquires data.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A system for controlling medical equipment during a medical procedure, comprising:
a passive radio frequency identification (RFID) tag comprising: an antenna; an RFID circuit; and a switching device coupled with at least one of the antenna and the RFID circuit for activating the passive RFID tag;
an RFID sensor for detecting the passive RFID tag;
a controller coupled with the RFID sensor, the RFID sensor providing a signal to the controller, the signal indicating activated activation of the passive RFID tag,
the passive RFID tag configured to control a piece of medical equipment,
the switching device comprising a touch sensor, the switching device configured to operate the passive RFID tag at an operational frequency in response to a touch detected by the touch sensor, and
the passive RFID tag experiencing a change in at least one frequency property in response to the touch detected by the touch sensor; and
a surgical glove interface disposed within a surgical glove and configured to adaptively switch output selection, the passive RFID tag coupled with the surgical glove interface, wherein detection of a piece of medical equipment sets an output in relation to each button of the piece of medical equipment.

2. The system of claim 1, wherein the piece of medical equipment comprises a surgical tool.

3. The system according to claim 2, wherein the passive RFID tag is coupled with the surgical tool.

4. The system of claim 2, wherein at least one of:
the surgical tool comprises a pair of forceps and the passive RFID tag is configured to control the pair of forceps for performing cauterization;
the surgical tool comprises a resection device and the passive RFID tag is configured to control the resection device for performing at least one of: suction, tissue removal, and tissue manipulation;
the surgical tool comprises a drill and the passive RFID tag is configured to control operation of the drill; and
the surgical tool comprises a Raman imaging probe and the passive RFID tag is configured to control the probe for data acquisition.

5. The system according to claim 1, wherein the switching device is coupled with both the antenna and the RFID circuit, the switching device configured to at least one of couple and decouple the antenna in relation to the RFID circuit, whereby the passive RFID tag is respectively activated and deactivated.

6. The system according to claim 1, wherein the switching device is configured to switch the passive RFID tag between transmission of a first identification (ID) and transmission of a second ID.

7. The system according to claim 1, wherein the passive RFID tag is configured to transmit an identification (ID) in response to the touch detected by the touch sensor.

8. The system according to claim 1, wherein the passive RFID tag is configured to forgo transmission of an identification (ID) in at least one of: an absence of a detection of the touch detected by the touch sensor and a presence of the touch by the touch sensor.

9. The system according to claim 1, wherein the passive RFID tag comprises a sticker.

10. The system according to claim 1, wherein the passive RFID tag comprises a form that is wearable around a finger.

11. The system according to claim 1, wherein the piece of medical equipment comprises at least one of: a camera, an optical coherence tomography (OCT) device, an imaging device, a microscopy device, an exoscope, a display device, and a spectrometry device.

12. The system according to claim 1, wherein the passive RFID tag comprises a plurality of passive RFID tags configured for use in an operating room environment.

13. The system according to claim 12, wherein each passive RFID tag of the plurality of passive RFID tags comprises a distinct tactile pattern.

14. A medical system, comprising:
a controller;
at least one passive RFID tag comprising: an antenna; a touch sensitive RFID circuit;
and a switching device coupled with at least one of the antenna and the RFID circuit for activating the at least one passive RFID tag;
an RFID sensor configured to detect the at least one passive RFID tag, the RFID sensor coupled with the controller, the RFID sensor configured to transmit a signal to the controller in response to receiving a signal from the at least one passive RFID tag;
at least one piece of medical equipment,
the controller is configured to control the at least one piece of medical equipment in response to the signal from the RFID sensor; and
a surgical glove interface disposed within a surgical glove and configured to adaptively switch output selection, the at least one passive RFID tag coupled with the surgical glove interface, wherein detection of a piece of medical equipment sets an output in relation to each button of the piece of medical equipment.

15. The system according to claim 14, wherein the at least one passive RFID tag comprises a plurality of passive RFID tags, each passive RFID tag of the plurality of passive RFID tags is associated with a respective unique identifier, each respective unique identifier enabling the controller to distinguish each signal from each at least one passive RFID tag of the plurality of passive RFID tags.

16. The system according to claim 14,
wherein the at least one passive RFID tag comprises a plurality of passive RFID tags, and
wherein the controller is configured to transmit a control signal when a plurality of passive RFID tags is activated.

17. The system according to claim 14, further comprising a robotic arm having an end effector, wherein the at least one piece of medical equipment is coupled with the end effector.

18. The system according to claim 14, wherein the controller is further configured to write data to the at least one passive RFID tag, the data relating to the at least one piece of medical equipment controlled in response to the signal from the RFID sensor.

19. The system according to claim 18, wherein the data comprises data relating to at least one of: a number of times that the at least one piece of the medical equipment is used, whether the at least one piece of medical equipment is calibrated, or what procedure was performed using the medical equipment.

20. The system according to claim 14,
wherein the at least one piece of medical equipment comprises a surgical tool, and
wherein at least one of:
the surgical tool comprises a pair of forceps and the at least one passive RFID tag is configured to control the pair of forceps for performing cauterization;
the surgical tool comprises a resection device and the at least one passive RFID tag is configured to control the resection device for performing at least one of: suction, tissue removal, and tissue manipulation;
the surgical tool comprises a drill and the at least one passive RFID tag is configured to control operation of the drill; and
the surgical tool comprises a Raman imaging probe and the passive RFID tag is configured to control the probe for data acquisition.

\* \* \* \* \*